| United States Patent [19] | [11] | 4,051,320 |
|---|---|---|
| Yanagisawa et al. | [45] | Sept. 27, 1977 |

[54] PROCESS FOR PREPARING ALKOXYLATED DERIVATIVES OF CEPHALOSPORIN COMPOUNDS

[75] Inventors: Hiroaki Yanagisawa; Akiko Ando; Masami Fukushima; Hideo Nakao, all of Tokyo, Japan

[73] Assignee: Sankyo Company Limited, Tokyo, Japan

[21] Appl. No.: 592,947

[22] Filed: July 3, 1975

[30] Foreign Application Priority Data

July 24, 1974 Japan .................................. 49-85007

[51] Int. Cl.² .................. C07D 501/02; C07D 499/04
[52] U.S. Cl. ................................. 542/420; 260/239.1; 544/21
[58] Field of Search ....................... 260/243 C, 240 G

[56] References Cited

U.S. PATENT DOCUMENTS

| 3,843,641 | 10/1974 | Christensen et al. ............ 260/243 C |
| 3,867,379 | 2/1975 | Dolfini et al. ..................... 260/243 C |
| 4,016,155 | 4/1977 | Yanagisawa et al. ............. 260/243 C |

*Primary Examiner*—Nicholas S. Rizzo
*Attorney, Agent, or Firm*—Flynn & Frishauf

[57] ABSTRACT

Process for preparing 7-alkoxy cephalosporins useful as intermediates for various cephalosporin or penicillin derivatives which comprises reacting 7-benzylideneaminocephem or 6-benzylideneaminopenam compounds with a halide cation-producing compound in the presence of an alcohol and a base capable of forming a salt with a phenolic hydroxyl group or converting a phenolic hydroxyl group to phenolate ion.

7 Claims, No Drawings

PROCESS FOR PREPARING ALKOXYLATED DERIVATIVES OF CEPHALOSPORIN COMPOUNDS

This invention relates to a new process for preparing alkoxylated derivatives of β-lactam antibiotic substances. More particularly, it relates to a new process for introducing an alkoxy group into a cephem nucleus at the 7-position thereof or a penam nucleus at the 6-position thereof. Still more particularly, it is concerned with a new process for preparing an alkoxylated derivative of a β-lactam antibiotic substance having the formula

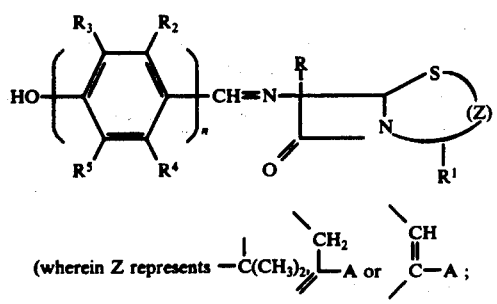

A and $R^1$ through $R^5$ represent groups which do not take part in the reaction: R represents an alkoxy group, preferably of 1 to 4 carbon atoms; and n is 1 or 2) which comprises reacting a compound having the formula:

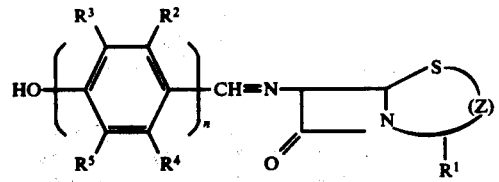

(wherein Z, A, $R^1$ through $R^5$ and n are the same as the above definition) with a halide cation-producing compound in the presence of an alcohol and a base which is capable of forming a salt with a phenolic hydroxyl group or converting a phenolic hydroxyl group to phenolate ion.

For introducing an alkoxy group into a cephem nucleus at its 7-position or into a penam nucleus at its 6-position, the following processes have been proposed in the art.

a. A process of diazotization of 7-aminocephalosporanic acid and subsequent conversion into the corresponding alkoxy derivative (Japanese Patent Provisional Publication No. 931/1972; Journal of the American Chemical Society, Vol. 94, p. 1408 (1972).

b. A process of alkylthiolation of fluorination and acylation of a 6- or 7-benzylideneamino compound and subsequent conversion into the alkoxylated compound (Journal of Organic Chemistry, Vol. 38, p. 943 and 2857 (1973).

c. A process of reaction of a 7-benzylideneamino compound with a dialkyl peroxy compound (Japanese Patent Provisional Publication No. 42691/1972).

d. A process wherein a 7-acylaminocephem compound or a 6-acylaminopenam compound is subjected to N-chlorination and converted to the corresponding acylimino compound followed by addition of methanol (Journal of the American Chemical Society, Vol. 95, p. 2401 and 2403 (1973)).

However, the above-mentioned prior art processes have some drawbacks in that, for instance, many reaction steps and complicated procedures are required with poor yields in the above process.

As a result of our research on alkoxylation of a cephem nucleus at its 7-position or a penam nucleus at its 6-position, we have found and developed an improved and simple method which entirely differs from the prior methods and is characterized by a skilful combination of a Schiff base type starting material with oxydation with a halide compound and alkoxylation.

It is, accordingly, a primary object of this invention to provide a new and improved process for preparing alkoxylated derivatives of β-lactam antibiotic substances (I).

Other objects and advantages of this invention will become apparent from the following disclosure of this invention.

The compounds (I) which may be prepared by the process of this invention are new substances not disclosed in the prior art and useful as an intermediate for the synthesis of various cephalosporin or penicillin derivatives each having a broad antibacterial spectrum.

For instance, the compounds obtained by the process of this invention can be reacted with an acylating agent directly or worked by existing steps, for example, by the action of 2,4-dinitrophenyl hydrazine and p-toluenesulfonic acid to form a 7-amino-7-methoxycephalosporin derivative, which is then reacted with an acylating agent to form a 7-methoxy-7-acylaminocephalosporin derivative followed by the removal of the protective group of carboxyl group at the 4-position in a conventional manner, whereby a compound having a strong antibacterial activity is produced.

More specifically, the starting compounds (II) which may be employed in the process of this invention are intended to include the two groups of compounds as defined below. The cephem compounds having the formula

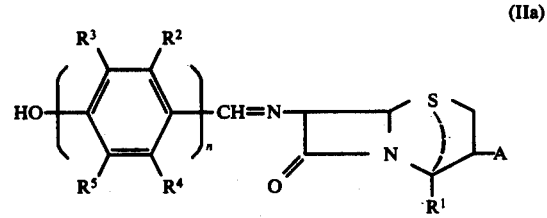

wherein A, $R^1$ through $R^5$ and n are as defined above; and the penam compounds having the formula

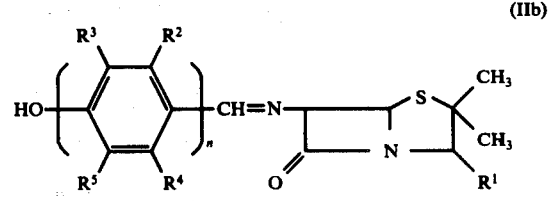

wherein $R^1$ through $R^5$ and n are as defined above.

In the above formulae (IIa) and (IIb), A and $R^1$ through $R^5$ can be any group which does not take part in the present reaction. The group represented by A is exemplified by the substitutent at 3-position of a conventional natural or synthetic cephem compound, and typically by hydrogen atom; methyl group; cyanomethyl group; azidomethyl group; an acyloxymethyl group, e.g. an alkanoyloxymethyl group having 3 to 6 carbon atoms such as acetoxymethyl, propionyloxymethyl or pivaloyloxymethyl, or an aroyloxymethyl group such as benzoyloxymethyl; carbamoyloxymethyl group; an alkoxymethyl group having from 2 to 5 carbon atoms such as methoxymethyl, ethoxymethyl or butyloxymethyl; an alkylthiomethyl group having from 2 to 5 carbon atoms such as methylthiomethyl, ethylthiomethyl, or propylthiomethyl; a heterocyclic thiomethyl group such as 2-pyridylthiomethyl, 2-(1,3,5-triazolyl)thiomethyl, 2-pyridyl-N-oxidothiomethyl, 3-pyrazolylthiomethyl, 1-imidazolylthiomethyl, 5-methyl-1,3,4-thiadiazolyl-2-thiomethyl or (1-methyl-1H-tetrazol-5-yl)thiomethyl; and the like. The group represented by $R^1$ is a group which does not take part in the reaction of the present process, and includes both a protected carboxyl group which can be converted to carboxyl group without breaking the cephem nucleus or the penam nucleus and a group which can be used as the product without ay conversion. Such a carboxyl-protecting group is exemplified by the groups which produce esters with the carboxylic acids, and includes a straight or branched chain lower-alkyl group having from 1 to 4 carbon atoms such as methyl, ethyl, propyl, isopropyl or butyl, and a lower-alkoxymethyl having from 2 to 5 carbon atoms or a benzyloxymethyl group such as methoxymethyl, ethoxymethyl, benzyloxymethyl or p-nitrobenzyloxymethyl; a lower-alkanoyloxy lower-alkyl group having from 3 to 8 carbon atoms such as acetoxymethyl, pivaloyloxymethyl, 1-acetoxyethyl, 1-acetoxypropyl or 1-pivaloyloxyethyl; benzoyloxymethyl group; cyanomethyl group; 2,2,2-trichloroethyl group; phthalimidomethyl group; a benzyl group such as benzyl, p-methoxybenzyl, p-nitrobenzyl or p-acyloxybenzyl; benzhydryl group; a phenacyl group such as phenacyl, p-bromophenacyl, p-methoxyphenacyl or p-nitrophenacyl; toluenesulfonylethyl group; a tri-lower-alkylsilyl group such as trimethylsilyl; and the like. An amido such as saccharimido

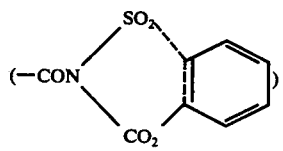

or the like is exemplified as another carboxyl-protecting group. The examples of the groups represented by $R^2$ through $R^5$ include hydrogen atom; a straight or branched chain lower-alkyl group having from 1 to 6 carbon atoms such as methyl, ethyl, propyl, isopropyl, butyl, isobutyl, tert-butyl, tert-pentyl or tert-hexyl; a lower-alkoxy group having 1 to 4 carbon atoms such as methoxy, ethoxy, propoxy, isopropoxy or tert-butoxy; a halogen atom such as chlorine or bromine; cyano group; a lower-alkoxycarbonyl group having from 2 to 5 carbon atoms such as methoxycarbonyl, ethoxycarbonyl or tert-butoxycarbonyl; phenyl group; a lower-alkanoyl group having from 2 to 5 carbon atoms such as acetyl, propionyl, butyryl or pivaloyl; an aroyl group having from 7 to 11 carbon atoms such as benzoyl, toluoyl or napthoyl; and the like. $R^2$ and $R^3$, and $R^4$ and $R^5$ may be joined with each other to form a carbocyclic or heterocyclic ring fused with the benzene ring to which they are bonded. Such polycyclic compounds include naphthalene, anthracene, indane, quinoline, benzofuran, indol, 2,3-dihydrobenzofuran, tetrahydronaphthalene and the like. $n$ is 1 or 2, and biphenyl, binaphthalene or p-(4-naphthyl)benzene is formed when $n$ is 2. Generally, it is preferable to employ a phenyl group having, at the ortho-position of the hydroxyl group, a sterically hindered alkyl group such as tert-butyl.

Of the above starting compounds (IIa) and (IIb), the three groups of the compounds having the following formulae are preferable:

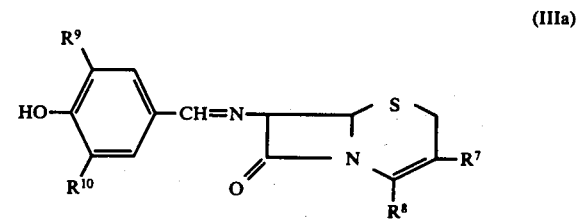

(IIIa)

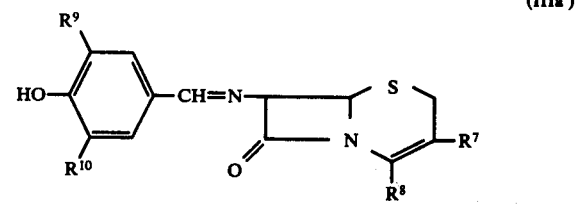

(IIIa')

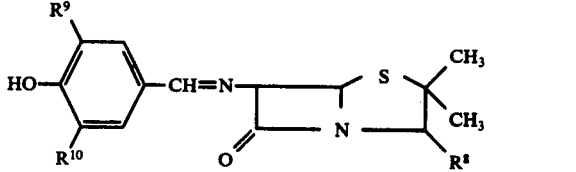

(IIIb)

In the above formulae, $R^7$ represents methyl group; a halomethyl group such as bromomethyl or chloromethyl; a lower-alkanoyloxymethyl group having 2 to 3 carbon atoms such as acetoxymethyl or propionyloxymethyl; azidomethyl group; a heterocylic thiomethyl group such as (1-methyl-1H-tetrazol-5-yl)thiomethyl, 5-methyl-1,3,4-thiadiazol-2-yl-thiomethyl or N-oxy-2-pyridylthiomethyl; or carbamoyloxymethyl group. $R^8$ represents pivaloyloxymethyl-oxycarbonyl group, 2,2,2-trichloroethyloxycarbonyl group, benzhydryloxycarbonyl group, p-bromophenacyloxycarbonyl group, tert-butoxycarbonyl group, p-methoxybenzyloxycarbonyl group or p-nitrobenzyloxycarbonyl group. $R^9$ and $R^{10}$ are the same or different groups and represent a lower-alkyl group having 1 to 5 carbon atoms such as methyl, ethyl, propyl, isopropyl, butyl, tert-butyl or tert-pentyl.

Of the above starting compounds (IIIa), (IIIa') and (IIIb), the compounds having the following formulae are most preferable:

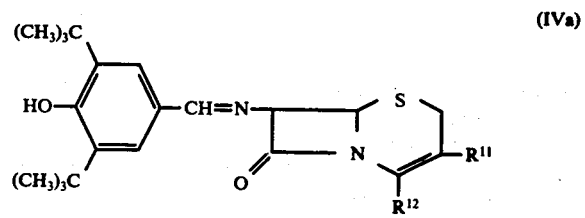

(IVa)

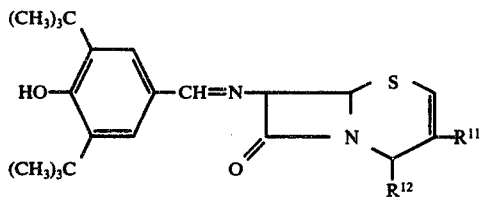

(IVa')

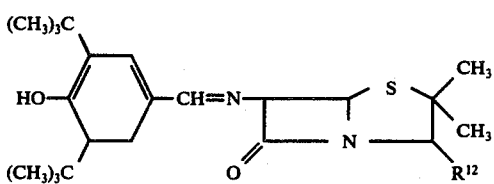

(IVb)

wherein R[11] represents methyl group, acetoxymethyl group, (1-methyl-1H-tetrazol-5-yl)thiomethyl or 5-methyl-1,3,4-thiadiazol-2-yl-thiomethyl group. R[12] represents tert-butoxycarbonyl group, benzhydryloxycarbonyl group, p-bromophenacyloxycarbonyl group, p-methoxybenzyloxycarbonyl group or 2,2,2-trichloroethyloxycarbonyl group.

Starting from any of the particularly indicated compounds having the above formulae (IIa), (IIb), (IIIa), (IIIa'), (IIIb), (IVa), (IVa') and (IVb), the process of this invention can be conducted in the same manner as in the starting compounds (II) to yield the corresponding 7- or 6-alkoxylated derivatives, respectively.

As explained above, the compounds (I) obtainable by the process of this invention are useful as intermediates for the synthesis of various cephalosporin or penicillin derivatives and those compounds (I) wherein R is an alkoxy group of 1 to 4 carbon atoms, particularly, methoxy group are especially valuable. Most preferable are the compounds having the formula

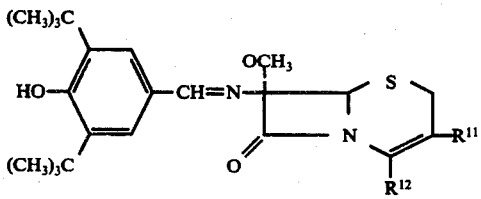

(V)

where R[11] and R[12] are as defined above.

In carrying out the process of this invention, a preferred embodiment thereof may comprise dissolving the starting material in a suitable solvent, adding thereto the alcohol, and then adding thereto the base which can form a salt or produce phenolate ions with phenol, followed by addition of a halide cation-producing compound.

A wide variety of halogen compounds which may be usually employed as a halogenating or oxidizing agent can be employed as the halide cation-producing compound in the process of this invention without specific limitation. Such compounds include a halogen simple substance such as chlorine or bromine; an N-halo-imide or -amide of a carboxylic acid such as N-chlorosuccinimide, N-bromosuccinimide, N-chloroacetamide, N-chlorophthalimide, N-bromophthalimide; an N-haloamide of a sulfonic acid such as N-chlorbenzenesulfonamide, N-bromobenzenesulfonamide, N-chloro-p-toluenesulfonamide or N-bromo-p-toluenesulfonamide; an N-haloaromatic nitrogen-containing heterocyclic compound, e.g. an N-halobenzotriazole such as 1-bromobenzotriazole, an N-halotriazine such as 1-chlorotriazine, or a halohydantoin such as N,N-dibromohydantoin; and an organic hypohalite, e.g. a lower-alkyl hypohalite such as tert-butylhypochlorite or tert-butylhypoiodite. Such lower alkyl hypohalite is preferably employed, and most generally tert-butylhypochlorite is employed.

A basic metallic compound and a basic nitrogen-containing compound may be employed in the process of this invention as the base which is capable of forming a salt of a phenolic hydroxyl group or converting a phenolic hydroxyl group to phenolate ion. Such basic metallic compounds include alkali metal compounds and alkaline earth metal compounds, e.g. the hydroxides such as potassium hydroxide and lithium hydroxide; the alkoxides such as lithium methoxide, sodium methoxide, potassium methoxide, lithium ethoxide, sodium ethoxide, potassium ethoxide, calcium ethoxide, potassium tert-butoxide, lithium cyclopropoxide, lithium propargyloxide, lithium benzyloxide and sodium benzyloxide; the hydride compounds such as lithium hydride, sodium hydride and calcium hydride; the metal hydrocarbons such as butyl lithium and phenyl lithium; and the like. The basic nitrogen-containing compounds include various species of amines, preferably tertiary-amines, e.g. tertiary-alkylamines such as trimethylamine, triethylamine and tributylamine; alicyclic amines such as N-methylpiperidine, N,N'-dimethylpiperidine, N-methylpyrrolidine and 1,8-diazabicyclo [5,4,0]-7-undecene; aromatic heterocyclic amines such as pyridine and picoline. Such alkali metal alkoxides are preferably employed, and the alkoxides having the alkoxyl group to be introduced are most preferably employed.

The alcohols employed in the process of this invention are those alcohols having the corresponding alkoxy groups to be introduced and may there be employed an aliphatic alcohol, an aromatic alcohol, an alicyclic alcohol and an araliphatic alcohol. Preferable groups of such alcohols include a lower-alkanol having 1 to 4 carbon atoms such methanol, ethanol, propanol, isopropanol, n-butanol or isobutanol; an unsaturated chain alcohol having 3 to 4 carbon atoms such as allyl alcohol, propagyl alcohol, 2-butanol or 2-butynol; a 3 to 7 membered-alicyclic alcohol such as cyclopropyl alcohol, cyclopentyl alcohol, cyclohexyl alcohol or cycloheptyl alcohol; and an araliphatic alcohol having a carbon chain of 1 to 3 carbon atoms bonded to the phenyl ring such as benzyl alcohol, phenetyl alcohol, phenylpropyl alcohol or cinnamyl alcohol. Methanol is most preferably employed in the process of this invention.

The solvents which may be employed in the reaction are not especially restricted unless they take part in the reaction and may be various species of inert organic solvents. The examples of such solvents include an ether such as diethyl ether, tetrahydrofuran, ethylene glycol dimethyl ether or diethylene glycol dimethyl ether; and a lower-fatty acid amide such as dimethyl formamide or dimethyl acetamide. Generally, tetrahydrofuran is preferably employed. The alcohol employed as a reagent in the reaction may also act as the solvent therefor when it is used in excess.

The reaction may be carried out by using stoichiometric amounts of the compounds which take part in the reaction. It is preferable, however, for 1 equivalent of the starting compound to employ the halide cation-producing compound in some excess, preferably in an amount of about 1.1–4 equivalents. It is preferable to add the base in the equivalent or rather excess amount, preferably about 1.1–2 equivalents, on the basis of the amount of the halide cation-producing compound. The alcohol may be usually employed in a great excess. The reaction temperature is not especially restricted; however, it is preferable to be relatively low in order to prevent side reactions. The reaction is usually conducted at room temperature or lower, especially at a temperature between 0° C and about −70° C. The reaction can be most preferably conducted at a temperature of −30° C. to −70° C, e.g., at a temperature provided with an alcohol (or acetone) -dry ice freezing mixture. The period of time required for the reaction mainly depends on the species of the starting compounds, reagents, alcohols and solvents employed, and the reaction temperature, and it generally ranges from several minutes to several hours.

After the reaction is completed, the desired product may be recovered from the reaction mixture according to a conventional method. For example, the pure desired product can be obtained by removing the solvent from the reaction mixture and then subjecting the residue to separation and purification according to a conventional method such as column chromatography using silica gel. The pure product can also be obtained by neutralizing the reaction mixture to the extent not to become strongly alkaline, immediately followed by pouring it into water, extracting the product with a suitable organic solvent, removing the solvent from the extract and then purifying the residue by means of a conventional method such as column chromatography using silica gel.

The process of this invention will be further explained by way of the working examples and the reference example. It should be understood, however, that the invention will not be restricted thereby.

EXAMPLE 1.

7β-(4-hydroxy-3,5-di-tert-butylbenzylideneamino)-7α-methoxy-3-acetoxymethyl-3-cephem-4-carboxylic acid benzhydryl ester In a mixture of 9 ml. tetrahydrofuran and 1 ml. methanol was dissolved 330 mg. 3-acetoxymethyl-7-(4-hydroxy-3,5-di-tert-butylbenzylideneamino)-3-cephem-4-carboxylic acid benzhydryl ester. The resulting solution was well cooled externally with an alcohol-dry ice freezing mixture and was added dropwise with stirring with a lithium methoxide solution prepared from 4 mg. lithium metal and 1 ml. methanol, followed by adding to the resulting reaction mixture a solution of 65 mg. tert-butylhypochlorite in 1 ml. tetrahydrofuran. Stirring was continued for 40 minutes after the addition and, then, the solvent was removed from the mixture under reduced pressure. The residue was subjected to column chromatography employing about 10 g. dry silica gel (prepared by drying, at about 120°–130° C for 3 hours in vacuum) and a mixture of cyclohexane-ethyl acetate (5:1) as the developer. By removing the solvent from the eluent under reduced pressure, 210 mg. of a yellow powder of the desired product was obtained.

Nuclear magentic resonance spectrum (CDCl₃)

δ : ppm
1.45 (singlet, C(CH₃)₃),
1.98 (singlet, 3-position —CH₂OCOCH₃),

-continued 3.35 (quartet, 2-position 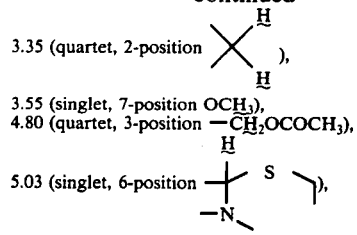), 3.55 (singlet, 7-position OCH₃),
4.80 (quartet, 3-position —CH₂OCOCH₃), 5.03 (singlet, 6-position 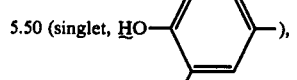), 5.50 (singlet, HO— 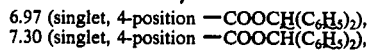 ), 6.97 (singlet, 4-position —COOCH(C₆H₅)₂),
7.30 (singlet, 4-position —COOCH(C₆H₅)₂), 7.63 (singlet, HO— 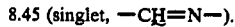 ), 8.45 (singlet, —CH=N—).
Thin-layer chromatography (silica gel): developer: n-hexane-ethyl acetate (3:1) R_f value: 0.4

The same reaction and treatment as those used in the above example were repeated except for using a solution of 76 mg. 1,8-diazabicyclo [5,4,0]-7-indecene (DBU) dissolved in 1 ml. tetrahydrofuran instead of the lithium methoxide solution prepared from 4 mg. lithium metal to produce the same desired product as that obtained in the above.

And, the same reaction and treatment as those used in the above example were repeated except that the reaction was effected at a temperature of 0°–3° C.; similar results were obtained.

EXAMPLE 2

7β-(4-hydroxy-3,5-di-tert-butylbenzylideneamino)-7α-methoxy-3-acetoxymethyl-3-cephem-4-carboxylic acid benzyhydryl ester In a mixture of 7 ml. tetrahydrofuran and 3 ml. methanol was dissolved 330 mg. 3-acetoxymethyl-7-(4-hydroxy-3,5-di-tert-butylbenzylideneamino)-3-cephem-4-carboxylic acid benzyhydryl ester. The resulting solution was externally cooled with an alcohol-dry ice freezing mixture and was added dropwise with stirring with a lithium methoxide solution prepared from 4 mg. lithium metal and 1 ml. methanol, followed by adding to the resulting reaction mixture the solution of 90 mg. N-bromosuccinimide dissolved in 2 ml. tetrahydrofuran. Stirring was continued for 2.5 hours after the addition and then the solvent was removed from the mixture under reduced pressure. By treating the residue in the same way as in Example 1, 200 mg. of the desired product was obtained. The product exhibits the same physico-chemical constants as those of the product obtained in Example 1.

The same reaction and treatment as those used in the above were repeated except for using 75 mg. of N-chlorosuccinimide, 70 mg. of N-bromoacetamide or 80 mg. of bromine instead of the N-bromosuccinimide to produce the same desired product as that obtained in the above example.

EXAMPLE 3

7β-(4-hydroxy-3,5-di-tert-butylbenzylideneamino)-7α-methoxy-3-methyl-3-cephem-4-carboxylic acid 2,2,2-trichlorethyl ester In a mixture of 7 ml. tetrahydrofuran and 3 ml. methanol was dissolved 281 mg. 7(4-hydroxy-3,5-di-tert-butylbenzylideneamino)-3-methyl-3-cephem-4-carboxylic acid 2,2,2-trichlorethyl ester. The resulting was externally cooled with an alcohol-dry ice freezing mixture and was dropwisely added with stirring with lithium methoxide solution prepared from 4 mg. lithium metal and 1 ml. methanol, followed by adding to the resulting reaction mixture a solution of 65 mg. tert-butylhypochlorite dissolved in 1 ml. tetrahydrofuran. Stirring was continued for 60 minutes after the addition and then the solvent was removed from the mixture under reduced pressure. The residue was subjected to column chromatography employing about 10 g. dry silica gel and a mixture of cyclohexane-ethyl acetate (8:1) as the developer. By removing the solvent under reduced pressure from the eluent, 220 mg. yellow powder of the desired product was obtained.

Nuclear magnetic resonance spectrum (CDCl$_3$) δ ppm:

1.45 (singlet, C . (C$\underline{H}_3$)$_3$),
2.21 (singlet, 3-position —C$\underline{H}_3$),
3.35 (quartet, 2-position),
3.60 (singlet, 7-position OC$\underline{H}_3$),
4.90 (quartet, 4-position —COOC$\underline{H}_2$CCl$_3$),
5.06 (singlet, 6-position),
5.55 (singlet, $\underline{H}$O—),
7.65 (singlet, HO—),
8.55 (singlet, —C$\underline{H}$=N—).

Thin-layer chromatography (silica gel): developer: cyclohexane - ether (2:1) R$_f$ value: 0.5

EXAMPLE 4

7β-(4-hydroxy-3,5-di-tert-butylbenzylideneamino)-7α-methoxy-(1-methyl-1H-tetrazol-5-yl)thiomethyl-3-cephem-4-carboxylic acid benzhydryl ester In a mixture of 7 ml. tetrahydrofuran and 3 ml. methanol was dissolved 356 mg. 7-(4-hydroxy-3,5-di-tert-butylbenzylideneamino)-3-(1-methyl-1H-tetrazol-5yl)-thiomethyl-3-cephem-4-carboxylic acid benzhydryl ester. The resulting solution was cooled with an alcohol-dry ice freezing mixture and was added dropwise with stirring with a lithium methoxide solution prepared from 4 mg. lithium metal and 1 ml. methanol, followed by adding to the reaction mixture a solution of 65 mg. tert-butylhypochlorite dissolved in 1 ml. dichlorethane. Stirring was continued for 50 minutes after the addition and, then, the solvent was removed from the mixture under reduced pressure. Then, the residue was subjected to colume chromatography employing about 10 g. dry silica gel and a mixture of cyclohexane-ethyl acetate (4:1) as the developer. By removing the solvent under reduced pressure from the eluent, 296 mg. yellow powder of the desired product was obtained.

Nuclear magnetic resonance spectrum (CDCl$_3$) δ ppm:

1.45 (singlet, C—(C$\underline{H}_3$)$_3$),
3.58 (singlet, 7-position —OC$\underline{H}_3$),
3.61 (singlet, 2-position),
3.79 (singlet, 3-position —S—),
4.31 (quartet, 3-position —C$\underline{H}_2$—S—),
5.09 (singlet, 6-position),
5.63 (singlet, $\underline{H}$O—),
6.98 (singlet, 4-position —COOC$\underline{H}$(C$_6$H$_5$)$_2$),
7.38 (singlet, 4-position —COOCH(C$_6$$\underline{H}_5$)$_2$),
7.72 (singlet, HO—),
8.60 (singlet, —C$\underline{H}$=N—).

Thin-layerchromatography (silica gel): developer: benzene-ethyl acetate (10:1) R$_f$ value: 0.4

EXAMPLE 5

6β-(4-hydroxy-3,5-di-tert-butylbenzylideneamino)-6α-methoxypenicillanic acid 2,2,2-trichloroethyl ester In a mixture of 7 ml. tetrahydrofuran and 3 ml. methanol was dissolved 282 mg. 6-(4-hydroxy-3,5-di-tert-butylbenzylideneamino) penicillanic acid 2,2,2-trichloroethyl ester. The resulting solution was cooled in an ethanol-dry ice bath and was added with stirring with a solution of 3.5 mg. lithium in 1 ml. methanol. After stirring for 10 minutes, the resulting reaction mixture was added to a solution of 65 mg. tert-butylhypochlorite in 1 ml. dichloroethane, followed by stirring for 1 hour. By concentrating the reaction liquid and purifying the resulting residue by means of chromatography using dry silica gel, 136 mg. 6β-(3,5-di-tert-butyl-4-hydroxy-benzylideneamino)-6α-methoxypenicillanic acid 2,2,2-trichloroethyl ester was obtained.

Infrared absorption spectrum Nujol ν max cm$^{-1}$: 3650, 1770, 1690, 1635

Nuclear magnetic resonance spectrum δ ppm (CDCL$_3$)

8.47 (1H, singlet, 6-position CH = N),
7.66 (2H, singlet, benzene ring H),
5.59 (1H, singlet, 5-position H),
4.78 (2H, singlet, CH₂CCl₃),
4.55 (1H, singlet, 3-position H),
3.55 (3H, singlet, 6-position OCH₃),
1.66 (3H, singlet, 2-position CH₃),
1.53 (3H, singlet, 2-position CH₃),
1.43 (18H, singlet, tert-butyl).

EXAMPLE 6

7β-(4-hydroxy-3,5-di-tert-butylbenzylideneamino)-7α-methoxy-3-methyl-2-cephem-4-carboxylic acid benzhydryl ester In a mixture of 20 ml. tetrahydrofuran and 10 ml. methanol was dissolved 1 g. 7β-(4-hydroxy-3,5-di-tert-butylbenzylideneamino)-3-methyl-2-cephem-4-carboxylic acid benzhydryl ester. The resulting solution was placed in an ethanol-dry ice bath and was added with stirring with a solution of 14 mg. lithium in 3 ml. methanol and then with a solution of 216 mg. tert-butylhypochlorite in 3 ml. tetrahydrofuran. After stirring a reaction mixture of 30 minutes and then concentrating it, the residue thus obtained was purified by means of column chromatography (3 × 33 cm, ethyl acetate-cyclohexane 1:5) using dry silica gel. Thus, there was obtained 100 mg. 7β-(4-hydroxy-3,5-di-tert-butylbenzylideneamino)-7α-methoxy-3-methyl-2-cephem-4-carboxylic acid bezhydryl ester.

Infrared absorption spectrum (CHCl₃) ν max cm⁻¹: 3650, 1765, 1745, 1690, 1660, 1630

Nuclear magnetic resonance spectrum δ ppm (CDCl₃):

8.42 (1H, singlet, CH = N),
7.60 (2H, singlet, 7-position benzene ring H),
7.24 (10H, singlet, COOCH(C₆H₅)₂),
6.83 (1H, singlet, COOCH(C₆H₅)₂),
5.83 (1H, broad, 2-position H),
5.54 (1H, singlet, benzene ring OH),
5.26 (1H, singlet, 6-position H),
4.81 (1H, broad, 4-position H),
3.45 (3H, singlet, 7-position OCH₃),
1.73 (3H, singlet, 2-position CH₃),
1.38 (18H, singlet, tert-butyl).

EXAMPLE 7

3-acetoxymethyl-7β-(3,5-di-tert-butyl-4-hydroxybenzylideneamino)-7α-methoxy-2-cephem-4-carboxylic acid benzhydryl ester An experiment was conducted according to the method in Example 6, using 3-acetoxymethyl-7β-(3,5-di-tert-butyl-4-hydroxxybenzylideneamino)-2-cephem-4-carboxylic acid benzhydryl ester. As a result, there was obtained 3-acetoxymethyl-7β-(3,5-di-tert-butyl-4-hydroxybenzylideneamino)-7α-methoxy-2-cephem-4-carboxylic acid benzhydryl ester in a yield of 31%.

Infrared absorption spectrum (CHCl₃) ν max cm⁻¹: 3650, 1770, 1745, 1635

Nuclear magnetic resonance spectrum δ ppm (CDCL₃)

8.43 (1H, singlet, CH = N),
7.62 (2H, singlet, 7-position benzene ring H),
7.24 (10H, singlet, COOCH(C₆H₅)₂),
6.83 (1H, singlet, COOCH(C₆H₅)₂),
6.26 (1H, broad, 2-position H),
5.51 (1H, singlet, benzene ring OH),
5.17 (1H, singlet, 6-position H),
5.08 (1H, broad, 4-position H),
4.47 (2H, singlet, 3-position — CH₂O — ),
3.39 (3H, singlet, 7-position OCH₃),
1.85 (3H, singlet, OCOCH₃),
1.37 (18H, singlet, tert-butyl).

EXAMPLE 8

7β-(4-hydroxy-3,5-diisopropylbenzylideneamino)-7α-methoxy-3-acetoxymethyl-3-cephem-4-carboxylic acid benzhydryl ester In a mixture of 5 ml. tetrahydrofuran and 3 ml. methanol was dissolved 206 mg. 7-(4-hydroxy-3,5-diisopropylbenzylideneamino)-3-acetoxymethyl-3-cephem-4-carboxylic acid benzhydryl ester. The resulting solution was cooled with an alcohol-dry ice freezing mixture and was added dropwise with stirring with a lithium methoxide solution prepared from 2.5 mg. lithium metal and 0.7 ml. methanol, followed by adding to the resulting reaction mixture a solution of 43 mg. tert-butylhypochlorite dissolved in 0.7 ml. dichloroethane. Stirring was continued for 60 minutes after the addition and, then, the solvent was removed from the mixture under reduced pressure. By treating the residue thus obtained in the same way as in Example 1, 84 mg. the desired product was obtained.

Nuclear magnetic resonance spectrum (CDCl₃) δ ppm:

1.30 (doublet, CH(CH₃)₂),
2.00 (quartet, 3-position —CH₂OCOCH₃),
3.14 (multiplet, CH(CH₃)₂),

3.42 (quartet, 2-position), 3.61 (singlet, 7-position —OCH₃),
4.88 (quartet, 3-position —CH₂OCOCH₃),

5.13 (singlet, 6-position), 7.03 (singlet, 4-position —COOCH(C₆H₅)₂),
7.41 (singlet, 4-position —COOCH(C₆H₅)₂),

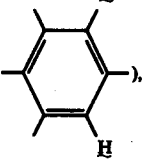
7.61 (singlet, HO—), 8.60 (singlet, —CH=N—),
Thin-layer chromatography (silica gel): developer: cyclohexane - ethyl acetate(3:1)
R/value: 0.3

EXAMPLE 9

7β-(4-hydroxy-3,5-di-tert-butylbenzylideneamino)-7α-methoxy-3-[2-(5-methyl-1,3,4-thiadiazolyl)thiomethyl]-3-cephem-4-carboxylic acid benzhydryl ester The same reaction and treatment as those used in the above Example 4 were repeated except that 300 mg. of 7-(4-hydroxy-3,5-di-tert-butylbenzylideneamino)-3-[2-(5-methyl-1,3,4-thiadiazolyl)thiomethyl]-3-cephem-4-carboxylic acid benzhydryl ester were employed, to give 75 mg. of the desired product as pale yellow powders.

Nuclear magnetic resonance spectrum (CDCl₃) δ :ppm 1.44 (singlet, C(CH₃)₃),
2.66 (singlet, 5-position CH₃ of 3-thiazole),
3.57 (singlet, 2-position H₂, 7-position OCH₃), 4.32 (quartet, 3-position-C$\underline{H}_2$S—),
5.06 (singlet, 6-position $\underline{H}$),
5.60 (singlet, phenolic O$\underline{H}$),
6.95 (singlet, COOC$\underline{H}$(C$_6$H$_5$)$_2$),
7.33 (singlet, COOCH(C$_6$$\underline{H}_5$)$_2$),
7.66 (singlet, 2,6-position H in benzene),
8.53 (singlet, —C$\underline{H}$ = N—).

Thin-layer chromatography (silica gel):Developer: cyclohexane-ethyl acetate (2:1)R$_f$ value: 0.4.

REFERENTIAL EXAMPLE

In 5 ml. dichloroethane was dissolved 200 mg. 7β-(4-hydroxy-3,5-di-tert-butylbenzylideneamino)-7α-methoxy-3-acetoxymethyl-3-cephem-4-carboxylic acid benzhydryl ester obtained in Example 1, followed by adding to the resulting solution 100 mg. thienylacetyl chloride. The resulting reaction mixture was stirred for 2 hours at room temperature, and then subjected to thin-layer chromatography for separation (silica gel: 20 × 20 cm, 0.2 cm in thickness, developer: ethyl acetate-benzene (1:4)), followed by extraction of the compound absorbed in the neighborhood of R$_f$ 0.45 using ethyl acetate. By removing the solvent under reduced pressure from the extract, there was obtained 60 mg. 7β-(2-thienylacetamido)-7α-methoxy-3-acetoxymethyl-3-cephem-4-carboxylic acid benzhydryl ester. The so obtained compound was dissolved in 0.6 ml. anisole, followed by adding to the resulting solution 0.3 ml. trifluoroacetic acid and stirring for 30 minutes under ice-cooling condition. Excess trifluoroacetic acid was removed under reduced pressure at room temperature. The residue was added with 3 ml. ethyl acetate, followed by extraction with 10% aqueous solution of dipotassium hydrogenphosphate. The extract was washed with ethyl acetate, adjusted to pH 2 with hydrochloric acid and then subjected to extraction with ethyl acetate. After washing with water, the extract was dried over anhydrous magensium sulfate. By removing the solvent under reduced pressure from the solvent, there was obtained 30 mg. 7β-(2-thienylacetamido)-7α-methoxy-3-acetoxymethyl-3-cephem-4-carboxylic acid.

What is claimed is:

1. A process for preparing a compound having the formula

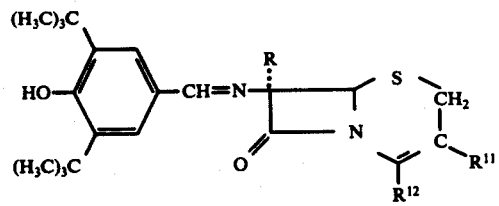

wherein
R$^{11}$ is methyl, acetoxymethyl, (1-methyl-1H-tetrazol-5-yl) thiomethyl or 5-methyl-1,3,4-thiadiazol-2-yl-thiomethyl;
R$^{12}$ is tert-butoxycarbonyl, benzhydryloxycarbonyl, p-bromophenacyloxycarbonyl, p-methoxybenzyloxycarbonyl or 2,2,2-trichloroethyloxycarbonyl; and
R is an alkoxy group having from 1 to 3 carbon atoms, which comprises contacting a compound having the formula

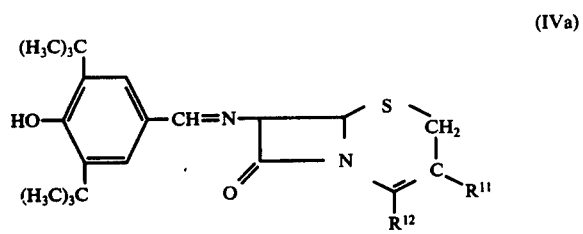

wherein R$^{11}$ and R$^{12}$ are as defined above, with from about 1.1 to about 4 equivalents of a halide cation-producing compound per equivalent of said compound of formula (IVa), in the presence of a lower alkanol having from 1 to 4 carbon atoms and from about 1.2 equivalents to about 2 equivalents of a base per equivalent of said compound of formula (IVa), at a temperature of from about 0° C. to about −70° C., said halide cation-producing compound being selected from the group consisting of a halogen, N-chlorosuccinimide, N-bromosuccinimide, N-chloroacetamide, N-chlorphthalimide, N-bromophthalimide, N-chlorbenzenesulfonamide, N-bromobenzenesulfonamide, N-chloro-p-toluenesulfonamide, N-bromo-p-toluenesulfonamide, 1-bromobenzotriazole, 1-chlorotriazine, N,N-dibromohydantoin, tert-butylhypochlorite and tert-butylhypoiodite, and said base being selected from the group consisting of an alkali metal hydroxide, an alkaline earth metal hydroxide, lithium methoxide, sodium methoxide, potassium methoxide, lithium ethoxide, sodium ethoxide, potassium ethoxide, calcium ethoxide, potassium tert-butoxide, lithium cyclopropoxide, lithium propargyloxide, lithium benzyloxide, sodium benzyloxide, lithium hydride, sodium hydride, calcium hydride, butyl lithium, phenyl lithium, trimethylamine, triethylamine, tributylamine, N-methylpiperidine, N,N'-dimethylpiperidine, N-methylpyrrolidine, 1,8-diazabicyclo-[5,4,0]-7-undecene, pyridine and picoline.

2. The process of claim 1, wherein the halide cation-producing compound is a halogen.

3. The process according to claim 1, wherein said halide cation-producing compound is tert-butylhypoiodite.

4. The process according to claim 1, wherein said halide cation-producing compound is tert-butylhypochlorite.

5. The process according to claim 1, wherein said base is an alkali metal methoxide.

6. The process according to claim 1, wherein said alkanol is methanol.

7. The process according to claim 1, wherein said halide cation-producing compound is tert-bytylhypochlorite, said base is lithium methoxide, said alkanol is methanol, and said reaction is effected at a temperature of from −30° C. to −70° C.

* * * * *